(12) United States Patent
Tsukuda

(10) Patent No.: US 6,340,470 B1
(45) Date of Patent: Jan. 22, 2002

(54) SOLUBLE ISOFLAVONE COMPOSITION AND METHOD FOR PREPARING THE SAME

(75) Inventor: Koji Tsukuda, Kishiwada (JP)

(73) Assignee: Matsutani Chemical Industries Co., Ltd., Hyogo-ken (JP)

( * ) Notice: Subject to any disclaimer, the term of this patent is extended or adjusted under 35 U.S.C. 154(b) by 0 days.

(21) Appl. No.: 09/474,807

(22) Filed: Dec. 29, 1999

(30) Foreign Application Priority Data

May 17, 1999 (JP) ............................................ 11-136226

(51) Int. Cl.⁷ .......................... A61K 47/00; A61K 6/00; A61K 7/00
(52) U.S. Cl. ...................... 424/439; 424/400; 424/401; 424/441; 424/195.11
(58) Field of Search .............................. 424/195.1, 401, 424/400, 439, 441

(56) References Cited

U.S. PATENT DOCUMENTS

| | | | |
|---|---|---|---|
| 4,428,972 A | * 1/1984 | Worzburg et al. | 426/578 |
| 4,826,963 A | 5/1989 | Stadler et al. | 536/103 |
| 5,043,326 A | 8/1991 | Stadler et al. | 514/58 |
| 5,792,503 A | 8/1998 | Gugger et al. | 426/634 |
| 6,060,070 A | * 5/2000 | Gorbach | 424/195.1 |

FOREIGN PATENT DOCUMENTS

| | | | |
|---|---|---|---|
| JP | 6-296462 | * 10/1994 | |
| JP | 9-309902 | 12/1997 | ........... C08B/37/16 |
| JP | 10-298175 | 11/1998 | ......... C07D/311/36 |
| WO | 00113513 | * 3/2000 | |

* cited by examiner

Primary Examiner—Thurman K. Page
Assistant Examiner—Charesse L. Evans
(74) Attorney, Agent, or Firm—Sughrue Mion, PLLC

(57) ABSTRACT

A soluble isoflavone composition comprises isoflavone and a solubilizing agent consisting of anhydrous or water-containing propylene glycol and/or octenyl succinate-treated starch. The soluble isoflavone composition is prepared by, for instance, a method which comprises the step of heating isoflavone and a solubilizing agent consisting of anhydrous or water-containing propylene glycol and/or octenyl succinate-treated starch in the presence of water to thus solubilize isoflavone in water. The soluble isoflavone composition of the present invention has high solubility in water, is easily dissolved in water and is stable over a long period of time.

10 Claims, No Drawings

SOLUBLE ISOFLAVONE COMPOSITION AND METHOD FOR PREPARING THE SAME

BACKGROUND OF THE INVENTION

The present invention relates to a soluble isoflavone composition, a method for the preparation of the same and foods comprising the same.

It has been elucidated, by recent studies, that isoflavone included in beans such as soybean is a substance exhibiting various physiological activities such as an estrogenic activity, an antioxidant effect, an antibacterial activity, an antitumorigenic or anticarcinogenic activity and an effect of inhibiting bone density-reduction and thus, the usefulness thereof has been reappreciated from the viewpoint of prevention of, for instance, various cancers or tumors such as breast cancer and prostate cancer and osteoporosis and from the viewpoint of improving or promoting health.

The Japanese people has conventionally been in the habit of eating a large quantity of processed bean foodstuffs such as soybean curd, soybean milk, dried bean curd, fermented soybeans, cooked beans, miso and soy sauce and therefore, the Japanese people has conventionally ingested a large quantity of isoflavone without the intention of taking the same. However, the quantity of isoflavone taken by the Japanese people has gradually been reduced because of the westernization of the eating habits of the Japanese people. This accordingly results in the reduction of the amount or frequency of eating such processed bean foods, or an increase in the number of such processed foods whose isoflavone content has been reduced because of, for instance, the palate of the Japanese people. This would in turn be considered to be a cause of, for instance, increased number of patients suffering from osteoporosis, which is often observed for women at the turn of life.

Isoflavone has been commercialized in the form of powder prepared by extracting it from raw materials such as soybeans. However, these powdery products are hardly soluble in water, have strong bitterness, a rough taste and astringency as well as gritty feeling. For this reason, these powdery products are considerably limited in the application to foods or the like and accordingly, there has been a demand for the improvement thereof.

As a method for such improvement, there has been proposed a method, which comprises encapsulating isoflavone into cyclodextrin to thus solubilize the same in water. For instance, Japanese Un-Examined Patent Publication (hereunder referred to as "J.P. KOKAI") No. Hei 9-309902 discloses isoflavone derivatives prepared by encapsulating isoflavone derivatives contained in soybeans or fermented soybeans into at least one of β-cyclodextrin and γ-cyclodextrin; and J.P. KOKAI No. Hei 10-298175 discloses a method for preparing easily water-soluble soybean isoflavone by bringing an extract obtained from raw soybeans into contact with cyclodextrin in an aqueous solution to thus remove impurities. Each beverage such as a fruit drink or juice comprise unique flavoring components, flavors are added to these beverages to distinguish one from another and/or fancy flavors are imparted thereto. If cyclodextrin is used, however, such flavoring components and fragrance-emitting components are also encapsulated into the same and this accordingly impairs the emission of the perfume peculiar to each particular drink. In addition, the isoflavone encapsulated into cyclodextrin suffers from problems in that it is not always sufficient in the solubility in water, even beverages, which must be transparent become turbid due to the addition of such encapsulated isoflavone and this accordingly results in the reduction of the commercial value of the beverages.

As has been described above in detail, the isoflavone, which is made soluble in water by the conventional method, suffers from such problems that it is still insufficient in solubility in water and that it is greatly limited in its application depending on the kinds of foods. For this reason, there has been a strong demand for the development of a soluble isoflavone composition free of such problems.

SUMMARY OF THE INVENTION

Accordingly, it is an object of the present invention to provide a soluble isoflavone composition, which has high solubility in water, is easily dissolved in water, stable over a long time period and can be incorporated into various kinds of foods without changing characteristic properties peculiar thereto.

It is another object of the present invention to provide a method for preparing the soluble isoflavone composition.

It is still another object of the present invention to provide a food comprising the foregoing soluble isoflavone composition.

The inventors of this invention have conducted various studies to solve the foregoing problems associated with the conventional techniques, have found that the foregoing objects can effectively be accomplished through the use of propylene glycol and/or octenyl succinate-treated starch as solubilizing agents and have thus completed the present invention on the basis of the foregoing finding.

According to an aspect of the present invention, there is provided a soluble isoflavone composition, which comprises isoflavone and anhydrous or water-containing propylene glycol and/or octenyl succinate-treated starch as a solubilizing agent.

When the solubilizing agent is anhydrous or water-containing propylene glycol, the weight ratio of isoflavone to propylene glycol preferably ranges from 1:100 to 10:100 and more preferably 1:100 to 7:100.

On the other hand, if octenyl succinate-treated starch is used as the solubilizing agent, the weight ratio of isoflavone to octenyl succinate-treated starch preferably ranges from 2:100 to 25:100 and more preferably 2:100 to 20:100.

Moreover, if the solubilizing agent used comprises a mixture of anhydrous or water-containing propylene glycol with octenyl succinate-treated starch, the weight ratio of isoflavone to propylene glycol preferably ranges from 1:100 to 10:100 and more preferably 1:100 to 7:100 and the weight ratio of isoflavone to octenyl succinate-treated starch preferably ranges from 2:100 to 25:100 and more preferably 2:100 to 20:100.

The soluble isoflavone composition of the present invention is preferably in the form of a stock solution or powder.

According to another aspect of the present invention, there is provided a food comprising the foregoing soluble isoflavone composition. Specific examples of such foods include fruit juices, juices, sport drinks, soups, jellies, coffee and black tea.

According to a further aspect of the present invention, there is provided a method for preparing a soluble isoflavone composition, which comprises the step of heating isoflavone and a solubilizing agent comprising anhydrous or water-containing propylene glycol and/or octenyl succinate-treated starch in the presence of water to thus solubilize isoflavone in water.

The heating temperature is not restricted to any specific range inasmuch as it is sufficient to dissolve isoflavone in water, but preferably ranges from 70 to 100° C., more preferably 80 to 95° C. and most preferably 85 to 95° C.

According to a still further aspect of the present invention, there is also provided a method for preparing a soluble isoflavone composition in the form of powder, which comprises the steps of heating isoflavone and a solubilizing agent consisting of octenyl succinate-treated starch in the presence of water to thus solubilize isoflavone in water and then drying the solution.

DESCRIPTION OF THE PREFERRED EMBODIMENTS

The term "isoflavone" is a general term for isoflavone derivatives such as daidzein, glycitin and genistein present in beans such as soybeans. It is quite difficult to isolate these isoflavone derivatives, in their pure conditions, from soybeans or the like and in many cases, they are put on the market in the form of mixtures containing, for instance, soybean saponin and/or soybean proteins. In the present invention, the term "isoflavone" is used to embrace mixtures containing, for instance, soybean saponin and/or soybean proteins, preferably those containing not less than 30% by weight of isoflavone, in addition to pure isoflavone.

Such isoflavone is prepared by, for instance, a method disclosed in J.P. KOKAI No. Hei 4-266898, which comprises pulverizing embryo axes of soybeans, extracting from the pulverized embryo axes three times with 70% water-containing alcohol, again extracting with a butanol-water mixed solvent and then drying; a method disclosed in J.P. KOKAIMNo. Hei 10-23878, which comprises the steps of heating an aqueous soybean molasses solution prepared by removing the ethanol from an ethanol to water extract of defatted soybean flakes, subjecting the aqueous solution to ultrafiltration to give a filtrate and separating isoflavone from the filtrate by cooling the same to thus recover the isoflavone; a method which comprises adsorbing isoflavone present in such an extract on an adsorbing resin and then eluting the isoflavone from the resin with an alcohol-water mixed solvent; or a method disclosed in J.P. KOKAI No. Hei 10-316671, which comprises removing the alcohol from an alcohol extract of soybeans or the like, solubilizing the isoflavone compounds through the addition of an alkali and then acidifying the solution to thus separate and recover the isoflavone compounds.

In the present invention, the term "solubilized isoflavone" means isoflavone obtained by treating untreated isoflavone hardly soluble in water with a solubilizing agent or isoflavone whose solubility in water is improved through such a treatment.

The present invention is characterized in that the solubilizing agent used for solubilizing isoflavone comprises anhydrous or water-containing propylene glycol and/or octenyl succinate-treated starch.

If isoflavone is heated in anhydrous or water-containing propylene glycol at a temperature ranging from 70 to 100° C., preferably 80 to 95° C. and more preferably 85 to 95° C., isoflavone is completely dissolved therein to give a transparent solution. This is because if the heating temperature is less than 70° C., isoflavone is not sufficiently dissolved in the anhydrous or water-containing propylene glycol and it is thus difficult to obtain a transparent solution, while even if the temperature exceeds 100° C., the transparency of the resulting solution is not improved any more.

The weight ratio of isoflavone to propylene glycol preferably ranges from 1:100 to 10:100 and more preferably 1:100 to 7:100.

The concentration of propylene glycol in the water-containing propylene glycol is not restricted to any particular range inasmuch as the amount of isoflavone dissolved therein is greater than the amount thereof capable of being solubilized in water, when heating isoflavone in the water-containing propylene glycol. When isoflavone is dissolved in the water-containing propylene glycol with heating, however, the solubility of isoflavone in the solubilizing agent abruptly increases at a propylene glycol concentration of about 20% by weight or higher, the solubility thereof reaches the maximum level at a propylene glycol concentration of about 80% by weight and isoflavone is soluble even in propylene glycol per se. For this reason, the propylene glycol concentration in the solubilizing agent preferably ranges from 20 to 100% by weight, more preferably 50 to 100% by weight and most preferably 60 to 100% by weight.

The solubilized isoflavone, i.e., the soluble isoflavone composition according to the present invention can easily provide an aqueous solution simply by addition thereof to water and the aqueous solution maintains its transparency when the temperature thereof is held at a level of not less than about 60° C. Moreover, the soluble isoflavone composition of the present invention can be stored over a long period of time and therefore, a desired amount thereof can be used at need. On the other hand, when storing the solution at room temperature or a low temperature in a refrigerator, the solution sometimes becomes turbid or forms precipitates of isoflavone, but the precipitates are very small in size and they can easily be dispersed, as compared with a dispersion obtained by simply suspending isoflavone in water.

Isoflavone may be dissolved in anhydrous or water-containing propylene glycol each time, but it is quite convenient that isoflavone is previously dissolved in anhydrous or water-containing propylene glycol to give a stock solution thereof and to store the same. The stock solution is in general stored at room temperature. In such case, the anhydrous or water-containing propylene glycol preferably has a propylene glycol concentration ranging from 60 to 100% by weight since the resulting isoflavone solution is stable even if it is stored over a long period of time.

The isoflavone solution thus obtained can maintain its transparency when it is heated, in particular, to a temperature of not less than 60° C. Therefore, if the composition of the present invention is added to a hot drink such as coffee, black tea or soup, the drink is not cloudy or does not cause any precipitation at all. In addition, the solution may form precipitates to some extent when storing it in a refrigerator, but the resulting precipitates are very small in size and can easily be dispersed in the solution. Therefore, when it is added to drinks such as fruit drinks, which are cloudy, by nature, any significant problem does not arise.

The octenyl succinate-treated starch used in the present invention, as a solubilizing agent is a product obtained by acting an esterifying agent such as anhydrous octenyl succinate on starch and includes octenyl succinate-treated starch whose molecular weight is reduced, as well.

The octenyl succinate-treated starch may be either hot water-soluble or cold water-soluble one. If isoflavone is used for general purposes, the size of the octenyl succinate-treated starch is not a serious problem, but when isoflavone is used in, for instance, drinks requiring high transparency, more preferably used is low molecular weight octenyl succinate-treated starch or one having a viscosity, as determined using a 20% by weight aqueous solution, ranging from 10 to 100 cp. If the viscosity of the aqueous solution is less than 10 cp, a greater amount of the solution is required for achieving the same effect, while if it exceeds 100 cp, the transparency of the resulting solution is slightly impaired. In this connection, the viscosity, as determined using a 20% by weight aqueous solution, is measured using a Brookfield rotational viscometer at a temperature of 30° C. The aqueous solution is prepared by dispensing 40 g of a sample and 160 g of water into a beaker having an inner volume of 200 ml to give an aqueous solution, in case of cold water soluble samples, or further heating the resulting-mixture up to 90° C., then cooling the resulting solution and compensating the loss of water due to evaporation, in case of hot water-soluble samples.

The molecular weight of the octenyl succinate-treated starch can be reduced by, for instance, a method for preparing soluble starch, which comprises acting an acid such as sulfuric acid or hydrochloric acid or an oxidizing agent such as sodium hypochlorite on starch in particulate states to thus decompose the starch; or a method for preparing maltodextrin, which comprises adding an acid such as oxalic acid or hydrochloric acid or amylase to starch and then heating the mixture to convert the starch into a glue and to thus decompose the same. Low molecular weight starch such as those soluble starch type ones are soluble in hot water, while those of maltodextrin type ones are soluble in cold water. In addition, the soluble starch type ones may be subjected to esterification after the decomposition. In this respect, the soluble starch type ones, which are soluble in hot water, may be converted into cold water-soluble ones by treating them with a drum dryer or an extruder.

Raw starch materials to be used are not restricted to any particular one and a variety of starches may be used. Specific examples thereof include naturally occurring starches such as potato starch, tapioca starch, wheat starch, cornstarch, waxy cornstarch, sago starch and glutinous rice starch; and processed starches such as those prepared by treating naturally occurring starches through various means such as bleaching and conversion into hydroxypropyl derivatives thereof.

If octenyl succinate-treated starch is used as the solubilizing agent, the weight ratio of isoflavone to octenyl succinate-treated starch preferably ranges from 2:100 to 25:100 and more preferably 2:100 to 20:100.

In this case, isoflavone can be solubilized by heating it in water containing octenyl succinate-treated starch in an amount of 4 to 50 times that of the isoflavone at a temperature preferably ranging from 70 to 100° C. and more preferably about 80 to 95° C. to thus give an aqueous-solution of isoflavone. The concentration of isoflavone in the aqueous solution is suitably limited to not more than about 1% by weight.

If the amount of an octenyl succinate-treated starch is less than 4 times that of isoflavone, it is sometimes difficult to obtain any transparent aqueous solution of isoflavone, while the use of an octenyl succinate-treated starch in an amount of more than 50 times that of isoflavone does not show any further effect of improving the stability of the resulting isoflavone aqueous solution. On the other hand, if the heating temperature is less than 80° C., in particular, less than 70° C., isoflavone is insufficiently dissolved in water and accordingly, a transparent solution cannot always be prepared, while the use of the heating temperature higher than 95° C. does not ensure any further effect of improving the transparency of the resulting aqueous solution.

The octenyl succinate-treated starch may be either hot water-soluble type ones or cold water-soluble type ones. Isoflavone and octenyl succinate-treated starch are added to water without any pre-treatment or these components in their powdery states are admixed together in advance and then dispersed in water prior to heat the dispersion. Alternatively, octenyl succinate-treated starch is first dissolved in water, then isoflavone is introduced into the resulting aqueous solution and thereafter the mixture is heated. In any case, it is important to heat isoflavone in the presence of octenyl succinate-treated starch.

The solubilized isoflavone aqueous solution thus prepared can effectively maintain its transparency over a long period of time irrespective of the manner of storage, for instance, storage at a high temperature, room temperature or a low temperature. Therefore, the aqueous solution is suitable for use in foods requiring high transparency such as consomme soup.

The isoflavone composition, which is made water-soluble by the use of an octenyl succinate-treated starch, can freely be diluted with water. Therefore, in the present invention, isoflavone can be used or stored in the form of a stock solution having a concentration higher than a desired one. In such case, the concentration of isoflavone, which can be solubilized in water, is relatively low on the order of up to about 0.2% by weight at a low temperature and up to about 1% by weight at a high temperature.

For this reason, the soluble isoflavone composition is more preferably used or stored in a powdery condition. The isoflavone composition may be powdered by, for instance, a method comprising the step of drying an isoflavone aqueous solution having the highest possible concentration and prepared by the foregoing method. Drying methods usable herein may be any conventionally known drying methods such as lyophilization (or freeze-drying), spray drying and drying in a drum dryer. At this stage, it is also possible, as a means for improving the drying efficiency, to add, to the isoflavone solution, at least one member suitably used as ingredients of each desired food and selected from the group consisting of sugar, glucose, maltose, lactose, starch hydrolyzates decomposed to a DE value ranging from about 3 to 25 and hydrolyzates of reduced starch thereof, to thus increase the concentration of the aqueous solution prior to the drying step.

The powdered soluble isoflavone composition thus prepared is easily dissolved in both cold and hot water. The powdery composition can be stored over a long period of time and thus can be used in a desired amount at need. It is also possible to incorporate into fast foods such as soup, which can be regenerated simply by addition of hot water.

When solubilizing isoflavone using an octenyl succinate-treated starch as a solubilizing agent, it is necessary to heat these components, in the coexistence thereof and a problem arises, such that the concentration of isoflavone is rather too low to prepare a stock solution.

As a method for eliminating the foregoing problem, there may be listed, for instance, a method which comprises solubilizing isoflavone using both octenyl succinate-treated starch and propylene glycol. More specifically, the foregoing isoflavone is dissolved in anhydrous or water-containing propylene glycol to prepare an isoflavone solution having a relatively high concentration as a stock solution, and then adding the stock solution to an aqueous solution of octenyl succinate-treated starch to thus give an aqueous isoflavone solution, which has a relatively high isoflavone content and stability over a long period of time even when stored at a low temperature. The preliminary preparation of an aqueous solution of octenyl succinate-treated starch is quite convenient, since it can be added to the stock solution at any stage during the preparation of a food and at an arbitrary temperature. In this case, the ratio of the octenyl succinate-treated starch to isoflavone is preferably approximately identical to that used for solubilizing isoflavone using the succinate-treated starch because of the stability of the resulting solution.

When simultaneously using these anhydrous or water-containing propylene glycol and octenyl succinate-treated starch, a stock solution having a high isoflavone concentration can be prepared due to the use of propylene glycol and the resulting solution can be stored over a long period of time, while the use of the octenyl succinate-treated starch permits the saving of the time required for dissolving isoflavone each time and the maintenance of the stability of the aqueous solution even when it is kept in the cold storage and/or stored under acidic conditions. Therefore, the solution can be added to a wide variety of foods.

The isoflavone solution prepared using octenyl succinate-treated starch or the combination of octenyl succinate-treated starch and anhydrous or water-containing propylene glycol is excellent in transparency, never undergoes any change even when it is kept in cold storage over a long period of time and is suitable for use in a variety of foods, in particular, those requiring high transparency such as beverages or drinks and soups.

Incidentally, the amount of isoflavone required for the adult per day is believed to be about 40 mg as expressed in terms of the amount of the effective component. Isoflavone can be taken to a certain degree as the ordinary diet, but the correct amount thereof would considerably vary depending on the difference in race and eating habits. In addition, the intake of isoflavone has recently been reduced and has been lower than the foregoing required amount even in the Asian races, who are in habit of taking a wide variety of soybean foods, because of the wide spread of processed bean foods. The soluble isoflavone composition of the present invention can be added to foods such as drinks or soup to thus easily supplement a proper amount of isoflavone, whose intake is insufficient.

Accordingly, the foods containing the soluble isoflavone composition of the present invention preferably contain isoflavone in an amount ranging from about 5 to 40 mg per food usually taken per day.

Moreover, the water used for preparing the soluble isoflavone composition of the present invention may contain other components, for instance, sweeteners such as sugar, isomerized sugar, fruit sugar and synthetic sweeteners; a variety of fruit juices; acidulants; and flavors.

The present invention will hereinafter be described in more detail with reference to the following Reference Examples and working Examples, but the present invention is not restricted to these specific Examples at all. In the following Reference Examples and working Examples, the terms "part" and "%" mean "part by weight" and "% by weight", respectively unless otherwise specified.

REFERENCE EXAMPLE 1

To 125 parts of water maintained at 30° C., there was added 100 parts of glutinous rice starch to give a starch dispersion, followed by addition of a 3% sodium hydroxide aqueous solution to the dispersion with stirring to thus maintain the pH value of the dispersion to 8 to 9, addition of 3 parts of anhydrous octenyl succinate to thus react them till the pH of the dispersion was not changed any more, neutralization thereof with a 5% by weight sulfuric acid solution, washing with water and dehydration of the resulting product. The dehydrated cake was dispersed in water to give a starch dispersion having a Baume degree of 18, followed by confirmation of whether the pH of the starch dispersion fell within the range: 6±0.2, addition of Crystase KD (α-amylase available from Daiwa Kasei KK) in an amount of 0.1% by weight on the basis of the amount of the starch, raising the temperature of the dispersion up to 85° C., allowing the dispersion at that temperature for 10 minutes, and then raising the temperature to 95° C. to thus liquefy the starch. The resulting aqueous solution was cooled to 87° C. and Crystase KD was added thereto in an amount of 0.1% by weight on the basis of the amount of the starch. The reaction was continued at 87±1° C. for 30 minutes, oxalic acid was added to the reaction system till the pH thereof reached 3.5 to thus inactivate the enzyme, followed by neutralization of the system with calcium carbonate, decoloration of the system using activated carbon and spray-drying the same to give octenyl succinate-treated starch whose 20% by weight aqueous solution had a viscosity of 25 cp.

Example 1

A desired amount of "NOVASOY" (isoflavone available from ADM Company in the United States; the content of effective component was found 50% by weight) was dispersed in 100 g of anhydrous or water-containing propylene glycol as shown in the following Table 1, and then the mixture was heated up to 86° C. to thus determine the maximum solubility thereof per 100 g of the anhydrous or water-containing propylene glycol. The results thus obtained are summarized in Table 1.

TABLE 1

| Concn. Of Propylene Glycol | Amt. Of NOVASOY Dissolved |
|---|---|
| — | Almost insoluble |
| 10% by weight | 0.5 g |
| 20% by weight | 1.25 g |
| 50% by weight | 6.5 g |
| 60% by weight | 8.5 g |
| 70% by weight | 9.5 g |
| 80% by weight | 10.0 g |
| 90% by weight | 7.5 g |
| 100% by weight | 4.8 g |

Example 2

An amount of 7 g of "NOVASOY" was dispersed in 100 g of water-containing propylene glycol having a concentration of 80% by weight, followed by heating them up to 86° C. according to the same manner used in Example 1 to thus dissolve the "NOVASOY" and to give a transparent solution. The solution was cooled to room temperature and then stored for one month. As a result, it was confirmed that the solution maintained its transparency.

Example 3

An amount of 4 g of "NOVASOY" was dispersed in 100 g of anhydrous or water-containing propylene glycol as shown in the following Table 2, followed by heating them up to 86° C. according to the same procedures used in Example 1 to thus dissolve the "NOVASOY" and to give a transparent solution. The solutions were stored at room temperature for one month. The conditions of the solutions observed after the storage for one month are shown in Table 2.

TABLE 2

| Concn. Of Propylene Glycol | Condition of the Solution After Storage |
| --- | --- |
| 50% by weight | A large amount of precipitates were formed and the solution was opaque. |
| 60% by weight | The solution did not cause any precipitation and was transparent. |
| 100% by weight | The solution did not cause any precipitation and was transparent. |

Example 4

Stock solutions were prepared using propylene glycol solutions having propylene glycol concentration of 60% and 100%, respectively and used in Example 3. These isoflavone stock solutions were stored at room temperature over one month and then they were diluted 10 times with 10 water maintained at 70° C. As a result, the diluted stock solutions each was found to be a transparent solution in which isoflavone was completely dissolved.

Example 5

To 100 g of water, there were added the octenyl succinate-treated starch prepared in Reference Example 1 and "NOVASOY" in amounts specified in the following Table 3, followed by heating them up to 85° C., then cooling the same to room temperature and observation of the conditions of these solutions. The results thus obtained are listed in Table 3.

TABLE 3

| Amt. Of Octenyl Succinate-Treated Starch | Amt. Of NOVASOY | Condition of Solution |
| --- | --- | --- |
| — | 20 mg | considerably opaque |
| 100 mg | 25 mg | almost transparent |
| 100 mg | 20 mg | transparent |
| 1000 mg | 50 mg | transparent |
| 5000 mg | 150 mg | transparent |

Example 6

To 90 parts of water, there were added, with stirring, 0.1 part of the octenyl succinate-treated starch prepared in Reference Example 1 and 0.02 part of "NOVASOY", the resulting mixture was heated to 85° C. to dissolve them, followed by addition of 6 parts of fruit sugar, 0.06 part of malic acid and 0.036 part of tartaric acid, in order, to the resulting solution, mixing them and then addition of water to a final volume of 100 parts to thus give a juice.

The resulting juice was stored in a refrigerator at a temperature ranging from 4 to 7° C. for one month and thereafter, the condition of the juice was examined. As a result, the juice was found to be excellent in transparency. The juice comprises isoflavone in an amount of 10 mg per 100 g as expressed in terms of the amount of the effective component and therefore, 20 mg of isoflavone, as the effective component, can be supplemented by taking, for instance, 200 g of the juice.

Example 7

To 95 parts of water-containing propylene glycol containing 85% by weight of propylene glycol, there was added 5 parts of "NOVASOY", followed by heating the mixture up to 85° C. to dissolve the "NOVASOY" and to thus give a 5% "NOVASOY" solution, and cooling the solution to room temperature.

To 85 parts of water, there was added, with stirring, 0.5 part of the octenyl succinate-treated starch prepared in Reference Example 1 to thus dissolve the latter, one part of the foregoing 5% "NOVASOY" solution was added to and mixed with the resulting mixture, then 10 parts of sugar, 0.06 part of malic acid and 0.03 part of tartaric acid were in order added to and mixed with the foregoing mixture to thus dissolve them in the latter and water was added thereto to the total amount of 100 parts to give a juice. The resulting juice was stored in a refrigerator at a temperature ranging from 4 to 7° C. for one month and thereafter, the condition of the juice was examined. As a result, the juice was found to be excellent in transparency. The juice comprises isoflavone in an amount of 25 mg per 100 g as expressed in terms of the amount of the effective component.

Example 8

To 670 parts of water, there were added, with stirring, 19 parts of the octenyl succinate-treated starch prepared in Reference Example 1 and one part of "NOVASOY", the resulting mixture was heated up to 850° C. to dissolve the "NOVASOY" and then the resulting "NOVASOY" solution was freeze-dried. An amount of 0.5 g of the resulting powder (containing isoflavone in a content of about 2.5% by weight as expressed in terms of the amount of the effective component) was introduced into 100 parts of water at ordinary temperature and then stirred. As a result, it was found that the powder was rapidly dissolved in water to give a transparent solution.

Example 9

To 170 parts of water, there were added, with stirring, 19 parts of the octenyl succinate-treated starch prepared in Reference Example 1, 5 parts of "TK-16" (maltodextrin available from Matsutani Chemical Industry Co., Ltd. having a DE value of about 17) and one part of "NOVASOY", the resulting mixture was heated up to 94° C. to dissolve the "NOVASOY" and then the resulting "NOVASOY" solution was subjected to spray-drying. An amount of 0.5 g of the resulting powder (containing isoflavone in a content of about 2% by weight as expressed in terms of the amount of the effective component) was introduced into 100 parts of water at ordinary temperature and then stirred. As a result, it was found that the powder was rapidly dissolved in water to give a transparent solution.

Example 10

To a pan, there were added 5 parts of the octenyl succinate-treated starch prepared in Reference Example 1 and 0.5 part of "NOVASOY", the resulting mixture was heated up to 85° C. using a gas heater to dissolve the "NOVASOY", followed by addition of raw materials as shown in the following Table 4, boiling the mixture well for 20 minutes and addition of water to the total amount of 1000 parts to thus give consomme soup seasoned with chicken extract. The resulting soup was excellent in transparency and was quite tasty.

TABLE 4

| | |
|---|---|
| Chicken Stock | 120 parts |
| Onion | 100 parts |
| Thyme (herb powder) | 0.01 part |
| Laurier (herb powder) | 0.02 part |
| Clove (herb powder) | 0.01 part |
| Black Pepper | 0.02 part |
| Common salt | 8 parts |
| Dextrose | 4 parts |
| Sodium Glutamate | 1.4 parts |

As has been described above in detail, the soluble isoflavone composition of the present invention has high solubility in water, is easily soluble in water and is stable over a long period of time.

What is claimed is:

1. A soluble isoflavone composition comprising isoflavone and a solubilizing agent consisting of (i) octenyl succinate-treated starch or (ii) a mixture of anhydrous or water-containing propylene glycol and octenyl succinate-treated starch.

2. The soluble isoflavone composition of claim 1 wherein the solubilizing agent is octenyl succinate-treated starch and the weight ratio of the isoflavone to the octenyl succinate-treated starch ranges from 2:100 to 25:100.

3. The soluble isoflavone composition of claim 1 wherein the solubilizing agent is a mixture of anhydrous or water-containing propylene glycol and octenyl succinate-treated starch, the weight ratio of the isoflavone to the propylene glycol ranges from 1:100 to 10:100 and the weight ratio of the isoflavone to the octenyl succinate-treated starch ranges from 2:100 to 25:100.

4. The soluble isoflavone composition of claim 1, 2 or 3 wherein it is in the form of powder.

5. A food comprising the soluble isoflavone composition as set forth in of any one of claims 1, 2, 3 or 4.

6. A method for preparing a soluble isoflavone composition, comprising the step of heating isoflavone and a solubilizing agent consisting of (i) octenyl succinate-treated starch or (ii) a mixture of anhydrous or water-containing propylene glycol and octenyl succinate-treated starch in the presence of water to thus solubilize isoflavone in water.

7. The method for preparing a soluble isoflavone composition as set forth in claim 6 wherein the heating temperature is not less than 70° C.

8. A method for preparing a soluble isoflavone composition in the form of powder, comprising the steps of heating isoflavone and a solubilizing agent consisting of octenyl succinate-treated starch in the presence of water to thus solubilize isoflavone in water and then drying the solution.

9. A method for preparing a soluble isoflavone composition, comprising the steps of dissolving isoflavone in anhydrous or water-containing propylene glycol to prepare an isoflavone solution having a relatively high concentration as a stock solution, and then adding the stock solution to an aqueous solution of octenyl succinate-treated starch to thus give an aqueous isoflavone solution.

10. A method for preparing a soluble isoflavone composition in the form of powder, comprising the steps of dissolving isoflavone is anhydrous or water-containing propylene glycol to prepare an isoflavone solution having a relatively high concentration as a stock solution, adding the stock solution to an aqueous solution of octenyl succinate-treated starch to thus give an aqueous isoflavone solution, and then drying the aqueous isoflavone solution.

* * * * *